United States Patent [19]
Jacobs

[11] Patent Number: 6,020,396
[45] Date of Patent: Feb. 1, 2000

[54] BONE CEMENT COMPOSITIONS

[75] Inventor: Christopher R. Jacobs, Hershey, Pa.

[73] Assignee: The Penn State Research Foundation, University Park, Pa.

[21] Appl. No.: 09/042,067

[22] Filed: Mar. 13, 1998

[51] Int. Cl.[7] .............................. A61L 25/00; C08L 31/02
[52] U.S. Cl. ...................... 523/116; 523/117; 524/533; 522/69; 623/16 C
[58] Field of Search ..................... 523/113, 116, 523/117; 524/533; 522/69; 623/16 C

[56] References Cited

U.S. PATENT DOCUMENTS

| | | | |
|---|---|---|---|
| 4,059,684 | 11/1977 | Gross et al. | 424/18 |
| 4,064,566 | 12/1977 | Fletcher et al. | 3/1.9 |
| 4,093,576 | 6/1978 | deWijn | 260/17 |
| 4,404,327 | 9/1983 | Crugnola et al. | 523/115 |
| 4,554,686 | 11/1985 | Baker | 623/16 |
| 4,668,295 | 5/1987 | Bajpai | 106/85 |
| 4,837,279 | 6/1989 | Arroyo | 525/193 |
| 4,902,728 | 2/1990 | Pietsch et al. | 523/115 |
| 4,910,259 | 3/1990 | Kindt-Larsen et al. | 525/259 |
| 5,049,157 | 9/1991 | Mittelmeier et al. | 623/16 |
| 5,264,215 | 11/1993 | Nakabayashi et al. | 424/423 |
| 5,276,070 | 1/1994 | Arroyo | 523/117 |
| 5,334,626 | 8/1994 | Lin | 523/116 |
| 5,336,699 | 8/1994 | Cooke et al. | 523/115 |
| 5,512,610 | 4/1996 | Lin | 523/116 |
| 5,527,864 | 6/1996 | Suggs et al. | 525/444 |
| 5,795,922 | 8/1998 | Demian et al. | 523/117 |

OTHER PUBLICATIONS

A Reduced–Modulus Acrylic Bone Cement: Preliminary Results, *Journal of Orthopaedic Research*, 8:623–626 Raven Press, Ltd., New York, 1990.

*Primary Examiner*—Andrew E. C. Merriam
*Attorney, Agent, or Firm*—Thomas J. Monahan

[57] ABSTRACT

Improved bone cement compositions and method of fixing a prosthetic implant to a bone using said improved bone cement compositions. More particularly, bone cement compositions having enhanced fatigue strength and consequently an increased projected service life when placed in a patient to fix a prosthetic implant securely in place. Specifically, bone cement compositions comprising a conventional poly[(methyl methacrylate)-styrene] copolymer based bone cement consisting of a liquid component and a dry powder component, and poly(butyl methacrylate) powder wherein at least a trace but no more than 5 wt % of the dry powder component is replaced by an equal mass of the poly(butyl methacrylate) powder.

5 Claims, No Drawings

BONE CEMENT COMPOSITIONS

FIELD OF THE INVENTION

This invention relates to improved bone cement compositions and methods for preparing said compositions. More particularly, this invention is directed to bone cement compositions having enhanced fatigue strength and consequently an increased projected service life when placed in a patient to fix a prosthetic implant securely in place. Most preferably, this invention is directed to bone cement compositions comprising a poly[(methyl methacrylate)-styrene] copolymer based bone cement consisting of a liquid component and a dry powder component, and poly(butyl methacrylate) powder wherein at least a trace but no more than 5 wt % of the dry powder component is replaced by an equal mass of the poly(butyl methacrylate) powder.

BACKGROUND OF THE INVENTION

With the advent of acrylate based bone cements, joint replacements and other surgical procedures using bone cement have become commonplace.

In joint replacement procedures, a prosthetic implant is fixed to the patient's bone. Such procedures begin with the surgical removal of the diseased portion of a bone. The most often used technique for setting a prosthetic implant proceeds with the preparation of the bone tissue by making a cavity therein. The cavity is shaped to receive a securement portion of a prosthetic implant. Also, a number of shallow holes may preferably be made in the surface of the bone tissue adjacent to the site where the prosthetic device will ultimately be fixed. These shallow holes project out from the cavity and provide a void into which bone cement may subsequently flow and cure. The surfaces of the bone are then thoroughly cleansed of all blood, fatty marrow tissue, bone fragments, and the like. The bone cement is then placed in the attachment site by any known method. The bone cement ultimately fills the interstices between the bone and the securement portion of the prosthetic implant, thereby facilitating a strong mechanical interlock between the bone, the bone cement and the prosthetic implant. To facilitate a strong mechanical interlock, it is desirable that the bone cement is able to freely flow into the porous recesses of the bone and any surgically produced holes projecting from the cavity.

Conventional acrylate based bone cements are widely used by surgeons. These conventional acrylate based bone cements are generally supplied to the surgeon as two separate components, a liquid component and a powder component. The liquid component of the bone cement generally comprises a liquid mixture with monomeric methyl methacrylate as the principal constituent. The powder component of these bone cements generally comprises a dry powder mixture with the primary constituent being a [methyl methacrylate-styrene] copolymer.

The recommended manner by which the liquid and dry components of conventional bone cements are mixed involves emptying the powdered component into a sterile container followed by addition of the liquid component. The components are then mixed thoroughly until polymerization commences. The specific mixing time depends on the bone cement used; the atmospheric conditions in the operating room, i.e., the temperature; and the method to be used to administer the bone cement. For pressurized administration, the components are mixed for a period of time before being loaded into a suitable sterile syringe while still relatively non-viscous for injection into the prepared area. Alternatively, for manual administration, the components should be mixed until the mixture develops a dough-like consistency which does not stick to a surgical glove. The bone cement may then be formed into a suitable shape for placement in the prepared area.

If administered before the degree of polymerization of the bone cement has proceeded to a suitable extent, the bone cement will be too fluid, difficult to handle and may cause overflow problems wherein the bone cement enters undesirable locations inside the patient where it must latter be removed to avoid complications. If administered after the degree of polymerization is too advanced, the bone cement will be too viscous and will not flow into all the interstitial areas and porous recesses of the bone to which the prosthetic implant is to be fixed. Furthermore, the bone cement may cure before the surgeon has sufficient time to properly align the prosthetic implant. Thus, the mixing time is an important variable in prosthetic implant procedures utilizing bone cements.

The mechanical interlock between the bone, the bone cement and the prosthetic implant is prone to deteriorate with time. Namely, over time, prosthetic implants may show signs of loosening as a result of a break down in the mechanical interlock. Loosening most often occurs at the interface between the bone and the cured bone cement, i.e., at the bone/cement interface. Bone cement failure is believed to be the primary cause of loosening. Specifically, conventional bone cements exhibit a tendency to fail by brittle fracture and fatigue, thereby losing its ability to transmit load from the prosthetic implant to the bone. This increased stress ultimately results in the loosening of the prosthetic implant with concomitant joint dysfunction and patient pain.

Historically, upwards of 20% of all hip joint prosthetic implants require maintenance after about 10 years of service. Maintenance ordinarily involves the surgical removal of the prosthetic implant and the cured bone cement. Removal of the bone cement is difficult and time consuming, requiring the surgeon to grind, pick and scrape the bone cement from the interstitial areas and porous recesses in the bone. Furthermore, the surgical removal of the implant like any other surgical procedure is visited with threat of infection and/or other complications resulting from surgery. Consequently, this high incidence of required maintenance makes desirable the development of improved designs for the prosthetic implants and the composition of the bone cements used to fix them to a bone. Accordingly, improved bone cement compositions which increase the useful life of an implant are desirable.

It is believed that the useful lifetime of the affixation of a prosthetic implant is a function of the fatigue strength of the bone cement used to affix the implant. Accordingly, bone cements having improved fatigue strength are desirable.

Furthermore, regardless of the method of administration used, the administering surgeon determines how long to mix the constituents before administration based largely upon the surgeon's knowledge and experience with the given bone cement and its historic handling characteristics. Surgeons who frequently perform prosthetic implant procedures have generally become familiar with the specific handling characteristics of the given bone cement they use. Particularly, most experienced surgeons are able to recognize when the bone cement is ready for administration based upon its consistency. This ability to recognize when bone cement is ready for administration is a skill that surgeons develop over time with continued use and experience with a given bone cement. Accordingly, it is desirable to develop improved bone cement compositions which exhibit handling characteristics which are identical or nearly identical to the bone cements with which surgeons are familiar.

Previous attempts to improve the fatigue strength of conventional bone cements through the addition of materials such as carbon fibers, glass fibers, silica, alumina, boron fibers, and the like have proven to be largely unsuccessful for a variety of reasons. For example, such fibers have been observed to cause a drastic reduction in the flow characteristics of the bone cements into which they are incorporated. Specifically, the fibers have been observed to block the flow of the bone cement into the interstitial areas and porous recesses in the bone and any surgically produced holes projecting from the cavity into which the prosthetic implant is to be fixed. This reduction in flow characteristics is believed to result in a poor mechanical interlock between the bone and the prosthetic implant.

SUMMARY OF THE INVENTION

In accordance with the present invention, it has been found advantageous to incorporate small amounts of poly (butyl methacrylate) into conventional acrylate based bone cements. Specifically, it has been found that the fatigue strength of conventional acrylate based bone cements may be significantly enhanced through the incorporation of poly (butyl methacrylate). Particularly, it has been found advantageous to replace a small amount of the dry powder component of a conventional acrylate based bone cement with poly(butyl methacrylate) powder, preferably resulting in a dry powder component comprising no more than 5 wt % poly(butyl methacrylate), preferably no more than 1 wt %, most preferably less than 1 wt %.

The bone cement compositions of the invention exhibit a fatigue strength (measured in cycles to failure using a fully-reversed tension-compression test at 15 MPa stress level in an enclosed, recirculating, normal saline environment at 37° C.) at least 280% greater than that exhibited by the corresponding conventional bone cements.

The bone cement compositions of the invention exhibit handling characteristics which are identical or nearly identical to the handling characteristics of the corresponding conventional bone cements.

The bone cement compositions of the invention exhibit flow characteristics which are virtually identical to the flow characteristics of the corresponding conventional bone cements. Moreover, the bone cement compositions of the invention flow freely into the porous recesses of the bone and any surgically produced holes projecting from the cavity into which the prosthetic implant is to be fixed.

It will be understood that the bone cement compositions of the invention may contain the additives conventionally used in this field. For instance, the powder component may contain, for example, X-ray contrast materials, polymerization initiators, antibiotics and antiseptics. Similarly, the liquid component may contain, for example, crosslinking agents, polymerization inhibitors, activators and coloring agents.

DETAILED DESCRIPTION OF THE PREFERRED EMBODIMENTS OF THE INVENTION

The bone cement compositions of the invention comprise a liquid component and a dry component which are admixed and dispensed in conventional manner using known equipment and methods.

The liquid component of the bone cement composition of the instant invention comprises a liquid monomer of an acrylic ester, preferably an acrylate having a $C_1$–$C_4$ alkyl group in the ester moiety, most preferably monomeric methyl methacrylate.

The liquid component of the instant invention may optionally contain a polymerization accelerator or activator. The activators used in the bone cement compositions of this invention may be selected from any of those known for use in this art. Particularly, activators suitable for use with the invention include, but are by no means limited to: N,N-dimethyl-p-toluidine; N,N-hydroxypropyl-p-toluidine; N,N-dimethyl-p-aminophen ethanol; N,N-dimethyl-p-toluidine; N,N-hydroxypropyl-p-toluidine and mixtures thereof; preferably N,N-dimethyl-p-toluidine. When present in the bone cement compositions of the instant invention, the activators preferably comprise 0.2 to 3.0 wt % of the liquid component, most preferably 0.4 to 1.0 wt %.

The liquid component may also optionally contain a free radical stabilizer or polymerization inhibitor. The polymerization inhibitors used in the bone cement compositions of this invention may be selected from any of those known for use in this art. Particularly, polymerization inhibitors suitable for use with the invention include, but are by no means limited to: hydroquinone, hydroquinonemonomethylether, ascorbic acid and mixtures thereof; preferably hydroquinone. When present in the bone cement compositions of the instant invention, the polymerization inhibitors preferably comprise 10 to 500 ppm of the liquid component, most preferably 20 to 100 ppm. The polymerization inhibitors function to prevent premature polymerization of the monomeric liquid acrylate which may otherwise occur upon exposure of the liquid component to heat, light or certain chemical reagents.

Most preferably, the liquid component of the bone cement compositions of the invention comprises: 97.4 to 99.25 vol % monomeric methyl methacrylate; 0.75 to 2.6 vol %; and 75±15 ppm hydroquinone.

The dry powder component of the bone cement compositions of the invention comprises no more than 5.0 wt % poly(butyl methacrylate), preferably no more than 1 wt % poly(butyl methacrylate). Most preferably, dry powder component of the bone cement compositions of the invention comprises a [methyl methacrylate-styrene] copolymer and no more than 1 wt % poly(butyl methacrylate). The dry powder component may also optionally contain poly(methyl methacrylate). Furthermore, it is believed that the bone cement compositions of the invention having less than 1 wt % poly(butyl methacrylate) will exhibit the greatest fatigue strength.

The dry powder component of the instant invention may also optionally contain an opacifying agent or X-ray contrast additive. The X-ray contrast additives suitable for use in the bone cement compositions of this invention may be selected from any of those known for use in this art. Particularly, X-ray contrast additives suitable for use with the instant invention include, but are by no means limited to: barium salts, e.g., barium sulphate; zirconium dioxide; zinc oxide; and mixtures thereof. When present in the bone cement compositions of this invention, the X-ray contrast additives preferably comprise 5 to 15 wt % of the dry powder component, most preferably 5 to 10 wt %. X-ray contrast additives are optionally included in the bone cement compositions of the invention to facilitate monitoring of the bone cement for loosening over time.

The dry powder component of the bone cement compositions of the instant invention may also optionally include an initiator. The initiators used in the bone cement compositions of this invention may be selected from any of those known for use in this art. Particularly, initiators suitable for use with the instant invention include, but are by no means limited to: benzoyl peroxide, lauroyl peroxide, methyl ethyl peroxide, diisopropyl peroxy carbonate and mixtures thereof. When present in the bone cement compositions of this invention, the initiators preferably comprise 0.5 to 3.0 wt % of the dry powder component.

The dry powder component of the bone cement compositions of the instant invention may also optionally include an antibiotic or antiseptic additive. The antibiotic or antiseptic additives used in the bone cement compositions of the invention may be selected from any of those known for use in this art. Particularly, antibiotic or antiseptic additives suitable for use with the instant invention include, but are by no means limited to: aminoglycosides, cephalosporins, macrolides, polymyxin-peptides, tetracyclines, fusidic acid, bacitracin/neomycin and mixtures thereof. When present in the bone cement compositions of this invention, the antibiotic or antiseptic additives preferably comprise 0.1 to 2.0 wt % of the dry powder component.

The dry powder component of the bone cement compositions of the invention may further optionally contain additives including colorants, catalysts, and the like.

Most preferably, the dry powder component compositions of the invention comprise: 71.25 to 87.5 wt % [methyl methacrylate-styrene] copolymer; 0 to 15.0 wt % poly (methyl methacrylate); 9.5 to 10.0 wt % barium sulfate; 0 to 2.5 wt % benzoyl peroxide; and no more than 1 wt % poly(butyl methacrylate).

The liquid component and the dry powder components of the bone cement compositions of the invention may be sterilized by any method of sterilization known for use in this art. Preferably, the liquid component is sterilized using bacteriological filtration. The dry powder component is preferably sterilized using irradiation techniques.

The ratio of the liquid component to the dry powder component on a volume (in ml) to mass (in g) basis is preferably 1 ml to 2 g.

In a preferred aspect, the invention comprises bone cement compositions based on modified conventional SIMPLEX® P bone cement. Conventional SIMPLEX® P bone cement is supplied to surgeons in a kit which comprises 20 ml of a liquid component and 40 g of a dry powder component. The liquid component of SIMPLEX® P consists of 97.4 vol. % monomeric methyl methacrylate, 2.6 vol. % N,N-dimethyl-p-toluidine, and 75±15 ppm hydroquinone. The dry component of SIMPLEX® P consists of 15.0 wt % poly(methyl methacrylate); 75.0 wt % [methyl methacrylate-styrene] copolymer; and 10.0 wt % barium sulfate.

The bone cement compositions of this aspect of the invention are produced by replacing at least a trace but no more than 2 g, preferably 0.4 g, of the dry powder component of conventional SIMPLEX® P with an equal mass of poly(butyl methacrylate) powder. The poly(butyl methacrylate) powder is mixed into the dry powder component. The mixture of poly(butyl methacrylate) powder and remaining dry powder component are subsequently processed in the same manner as unmodified SIMPLEX® P. Specifically, the dry powder mixture is placed in a sterile container. The liquid component is added to and mixed with the dry powder mixture. The components are mixed and administered as described in the background section herein.

In another preferred aspect, the invention comprises bone cement compositions based on modified conventional OSTEOBOND™ copolymer bone cement. Conventional OSTEOBOND™ copolymer bone cement is supplied to surgeons in a kit which comprises 10, 20 or 40 mL of a liquid component and 20, 40 or 80 g, respectively, of a dry powder component. The liquid component of OSTEOBOND™ copolymer bone cement consists of 99.25 vol. % monomeric methyl methacrylate, 0.75 vol. % N,N-dimethyl-p-toluidine, and 75±10 ppm hydroquinone. The dry component of OSTEOBOND™ copolymer bone cement consists of 87.5 wt % poly[(methyl methacrylate)-styrene] copolymer; 1.2 to 2.5 wt % benzoyl peroxide; and 10.0 wt % barium sulfate.

The bone cement compositions of this aspect of the invention are produced by replacing at least a trace but no more than 5 wt %, preferably 1 wt %, of the dry powder component of conventional OSTEOBOND™ copolymer bone cement with an equal mass of poly(butyl methacrylate) powder. The poly(butyl methacrylate) powder is mixed into the dry powder component. The mixture of poly(butyl methacrylate) powder and remaining dry powder component are subsequently processed in the same manner as unmodified OSTEOBOND™ copolymer bone cement. Specifically, the dry powder mixture is placed in a sterile container. The liquid component is added to and mixed with the dry powder mixture. The components are mixed and administered as described in the background section herein.

The handling characteristics of the bone cement compositions of the invention based on modified conventional bone cements are very similar to or indistinguishable from the handling characteristics of the unmodified conventional bone cements depending upon the mass of poly(butyl methacrylate) powder added thereto. Specifically, the lower the charge of poly(butyl methacrylate) powder the more indistinguishable the changes in handling characteristics become. Moreover, the currently preferred charge of poly (butyl methacrylate) powder in the bone cement compositions of the invention is no more than 1 wt % of the total mass of the dry powder component. At the preferred charge of no more than 1 wt %, the handling characteristics of the bone cement compositions of the invention have been observed to be indistinguishable from those of the corresponding unmodified conventional bone cements.

The bone cement compositions of the invention incorporating about 1 wt % poly(butyl methacrylate) powder exhibit fatigue strengths as much as 400% greater than those exhibited by the corresponding unmodified conventional bone cements.

The concepts of the invention will now be illustrated by the following Examples, which are intended to be purely exemplary and not limiting.

EXAMPLE 1

Test specimens made from a bone cement composition of the instant invention based on modifications to conventional SIMPLEX® P bone cement were produced (Composition A). The unmodified conventional SIMPLEX® P bone cement used to produce these test specimens, comprised:

(i) a 20 ml liquid component, consisting of: 97.4 vol. % monomeric methyl methacrylate, 2.6 vol. % N,N-dimethyl-p-toluidine, and 75±15 ppm hydroquinone; and, (ii) a 40 g dry powder component, consisting of: 15.0 wt. % poly(methyl methacrylate), 75.0 wt. % [methyl methacrylate-styrene] copolymer, and 10.0 wt. % barium sulfate (U.S.P.).

The test specimens of Composition A were prepared in the following manner:

(a) extracting 0.4 g of the 40.0 g SIMPLEX® P dry powder component, (b) mixing 0.4 g of poly(butyl methacrylate) powder procured from Aldrich® Chemical Company with the remaining 39.6 g of SIMPLEX® P dry powder component, (c) placing the mixture of dry powder into a sterile mixing bowl, (d) mixing the 20 ml SIMPLEX® P liquid component with the mixture of dry powder, (e) pouring the mixture produced in step (d) into a negative wax mold of a dumbbell-shaped geometry, (f) allowing the mixture to cure in the wax mold at 37° C. for at least 15 minutes, adding more mixture as necessary to compensate for contraction of the mixture during curing, (g) removing the cured test specimen of Composition A from the wax mold, (h) placing the cured test specimen into an ampule filled with normal saline solution, (i) aging the test specimen for at least seven (7) days in the normal saline solution while maintaining a temperature of about 37° C., and (j) recovering the aged test specimens.

The specimens produced by the above procedure were examined for inclusion of severe surface imperfections, such as craters or external bumps, etc. Any specimens exhibiting such imperfections were excluded from further analysis.

EXAMPLE 2

Test specimens made from a bone cement composition of the instant invention based on modifications to conventional SIMPLEX® P bone cement were produced (Composition B). The unmodified conventional SIMPLEX® P bone cement composition used to produce these test specimens, comprised:

(i) a 20 ml liquid component, consisting of: 97.4 vol. % monomeric methyl methacrylate, 2.6 vol. % N,N-dimethyl-p-toluidine, and 75±15 ppm hydroquinone; and, (ii) a 40 g dry powder component, consisting of: 15.0 wt. % poly(methyl methacrylate), 75.0 wt. % [methyl methacrylate-styrene] copolymer, and 10.0 wt. % barium sulfate (U.S.P.).

The test specimens of Composition B were prepared in the following manner:

(a) extracting 2.0 g of the 40.0 g SIMPLEX® P dry powder component, (b) mixing 2.0 g of poly(butyl methacrylate) powder procured from Aldrich® Chemical Company with the remaining 38.0 g of SIMPLEX® P dry powder component, (c) placing the mixture of dry powder into a sterile mixing bowl, (d) mixing the 20 ml SIMPLEX® P liquid component with the mixture of dry powder, (e) pouring the mixture produced in step (d) into a negative wax mold of a dumbbell-shaped geometry, (f) allowing the mixture to cure in the wax mold at 37° C. for at least 15 minutes, adding more mixture as necessary to compensate for contraction of the mixture during curing, (g) removing the cured test specimen of Composition B from the wax mold, (h) placing the cured test specimen into an ampule filled with normal saline solution, (i) aging the test specimen for seven (7) days in the normal saline solution while maintaining a temperature of about 37° C., and (j) recovering the aged test specimens.

The specimens produced by the above procedure were examined for inclusion of severe surface imperfections, such as craters or external bumps, etc. Any specimens exhibiting such imperfections were excluded from further analysis.

EXAMPLE 3

This example illustrates the enhanced fatigue strength exhibited by the bone cement compositions of the instant invention as compared to the corresponding unmodified conventional bone cement composition.

Specifically, test specimens were produced using conventional SIMPLEX® P bone cement, commercially available from Howmedica International Ltd. comprising:

(i) a 20 ml liquid component, consisting of: 97.4 vol. % monomeric methyl methacrylate, 2.6 vol. % N,N-dimethyl-p-toluidine, and 75±15 ppm hydroquinone; and, (ii) a 40 g dry powder component, consisting of: 15.0 wt. % poly(methyl methacrylate), 75.0 wt. % [methyl methacrylate-styrene] copolymer, and 10.0 wt. % barium sulfate (U.S.P.).

The test specimens of conventional SIMPLEX® P were prepared in the following manner:

(a) placing the 40.0 g of SIMPLEX® P dry powder component into a sterile mixing bowl, (b) mixing the 20 ml SIMPLEX® P liquid component with the 40.0 g of dry powder, (c) pouring the mixture produced in step (b) into a negative wax mold of a dumbbell-shaped geometry, (d) allowing the mixture to cure in the wax mold at 37° C. for at least 15 minutes, adding more mixture as necessary to compensate for contraction of the mixture during curing, (e) removing the cured test specimen of SIMPLEX® P from the wax mold, (f) placing the cured test specimen into an ampule filled with normal saline solution, (g) aging the test specimen for seven (7) days in the normal saline solution while maintaining a temperature of about 37° C., and (h) recovering the aged test specimens.

The specimens produced by the above procedure were examined for inclusion of severe surface imperfections, such as craters or external bumps, etc. Any specimens exhibiting such imperfections were excluded from further analysis.

Eighteen dumbbell-shaped specimens were subjected to fully-reversed tension-compression tests using a ±15 MPa stress level at 2 Hz in an enclosed, recirculating, normal saline environment at 37° C. Specifically, four specimens produced as described in Example 1 using Composition A, four specimens produced as described in Example 2 using Composition B and four specimens produce using conventional SIMPLEX® P produced as described above, were subjected to fatigue stress testing. Statistical analysis was carried out on the results of the above-described testing using a one-way Analysis of Variance. The Student-Newman-Keuls Multiple Comparison Test was then applied to obtain the p-values for each individual group to facilitate group comparisons. The results of the tests are listed in Table 1.

TABLE 1

| Bone<br>Cement Composition | No. of Specimens tested | Fatigue Strength<br>(cycles to failure)<br>w/standard deviation |
|---|---|---|
| Composition A | six (6) | 61,135 ± 32,059 |
| Composition B | six (6) | 42,807 ± 3,382 |
| SIMPLEX® P | six (6) | 15,054 ± 8,8308 |

It can be seen from the results of the testing that the bone cement compositions of the invention wherein 0.4 g and 2.0 g of the dry powder component of conventional SIMPLEX® P with 0.4 g and 2.0 g of poly(butyl methacrylate), respectively, produced bone cement compositions with an enhanced fatigue strength and, consequently an increased bone cement fatigue life. Specifically, a bone cement composition of the invention wherein 0.4 g of the dry powder component of conventional SIMPLEX® P was replaced with an equal mass of poly(butyl methacrylate) powder exhibited a fatigue strength 400% greater than that exhibited by unmodified SIMPLEX® P. A bone cement composition of the invention wherein 2.0 g of the dry powder component of conventional SIMPLEX® P was replaced with an equal mass of poly(butyl methacrylate) powder exhibited a fatigue strength 280% greater than that exhibited by unmodified SIMPLEX® P. Furthermore, while the handling characteristics of the bone cement of Composition B were slightly distinguishable from those of conventional SIMPLEX® P, the handling characteristics of the bone cement of Composition A were indistinguishable from those exhibited by conventional SIMPLEX® P.

It is believed that these and other aspects of the invention which will be readily apparent to those skilled in the art in view of the disclosures made herein will facilitate the production of bone cement compositions having enhanced fatigue strength and consequently an increased service life when placed in a patient to fix a prosthetic implant securely in place, thus resulting in a decreased need for required maintenance of the prosthetic implants.

The invention now having been disclosed in connection with the foregoing exemplary embodiments, additional embodiments will now be apparent to persons skilled in the art. The invention is not intended to be limited to the embodiments specifically mentioned, and accordingly reference should be made to the appended claims rather than the foregoing discussion, to assess the spirit and scope of the invention in which exclusive rights are claimed.

We claim:

1. A bone cement composition, comprising:

(a) a conventional poly((methyl methacrylate)-styrene) copolymer bone cement consisting of a liquid component and a dry powder component, and (b) poly(butyl methacrylate) powder; wherein at least a trace but no more than 1 wt % of the dry powder component is replaced by an equal mass of the poly (butyl methacrylate) powder.

2. The bone cement composition of claim 1, wherein the liquid component consists of about 20 ml of liquid, which consists essentially of:

(a) about 97.4 vol % monomeric methyl methacrylate, (b) about 2.6 vol % N,N-dimethyl-p-toluidine, and (c) 75±15 ppm hydroquinone, and wherein the dry powder component consists of about 40 g of dry powder, which consists essentially of:

(a) about 75.0 wt % (methyl methacrylate-styrene) copolymer, (b) about 15.0 wt % poly(methyl methacrylate), and (c) about 10.0 wt % barium sulfate.

3. The bone cement composition of claim 2, wherein the fatigue strength of the bone cement composition is at least 280% greater than the fatigue strength of the conventional poly((methyl methacrylate)-styrene) copolymer based bone cement.

4. The bone cement composition of claim 2, wherein the fatigue strength of the bone cement composition is at least 400% greater than the fatigue strength of the conventional poly((methyl methacrylate)-styrene) copolymer based bone cement.

5. The bone cement composition of claim 1, wherein the liquid component consists of about 10 ml of liquid, which consists essentially of:

(a) about 99.25 vol % monomeric methyl methacrylate,
    (b) about 0.75 vol % N,N-dimethyl-p-toluidine, and (c) 75±10 ppm hydroquinone, and wherein the dry powder component consists of about 20 g of dry powder, which consists essentially of:

(a) about 87.5 wt % poly((methyl methacrylate)-styrene) copolymer, (b) about 10.0 wt % barium sulfate, and (c) about 1.2 to 2.5 wt % benzoyl peroxide.

* * * * *